(12) United States Patent
Martens et al.

(10) Patent No.: US 7,253,331 B2
(45) Date of Patent: Aug. 7, 2007

(54) MOLECULAR SIEVE CATALYST COMPOSITION, ITS MAKING AND USE IN CONVERSION PROCESSES

(75) Inventors: Luc R. M. Martens, Melse (BE); Marcel J. Janssen, Kessel-Lo (BE); Machteld M. Mertens, Boortmeerbeek (BE); An Verberckmoes, Serskamp (BE); Guang Cao, Branchburg, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 507 days.

(21) Appl. No.: 10/844,168

(22) Filed: May 12, 2004

(65) Prior Publication Data

US 2005/0256354 A1    Nov. 17, 2005

(51) Int. Cl.
*C07C 1/00* (2006.01)
*B01J 27/182* (2006.01)
*B01J 29/04* (2006.01)

(52) U.S. Cl. ............... 585/640; 585/638; 585/639; 502/60; 502/64; 502/214; 502/439; 502/514; 423/DIG. 30

(58) Field of Classification Search ......... 585/638–640
See application file for complete search history.

(56) References Cited

U.S. PATENT DOCUMENTS

| | | | | |
|---|---|---|---|---|
| 3,902,993 A * | 9/1975 | Houser et al. | ............... | 209/166 |
| 4,025,572 A | 5/1977 | Lago | ........................ | 260/668 |
| 4,062,905 A | 12/1977 | Chang et al. | ............... | 260/682 |
| 4,079,095 A | 3/1978 | Givens et al. | ............... | 260/682 |
| 4,299,733 A | 11/1981 | Tu | ........................ | 252/455 Z |
| 4,310,440 A | 1/1982 | Wilson et al. | ............... | 252/435 |
| 4,440,871 A | 4/1984 | Lok et al. | ................... | 502/214 |
| 4,474,741 A | 10/1984 | Hoelderich et al. | ......... | 423/329 |
| 5,063,187 A | 11/1991 | Burgfels et al. | ............... | 502/71 |
| 5,316,656 A | 5/1994 | Pellet et al. | ................. | 208/120 |
| 5,367,100 A | 11/1994 | Gongwei et al. | ........... | 585/640 |
| 5,525,323 A | 6/1996 | Mueller et al. | ............. | 423/705 |
| 6,403,855 B1 * | 6/2002 | Mertens | ........................ | 585/640 |
| 6,503,863 B2 | 1/2003 | Fung et al. | ................. | 502/214 |
| 6,541,415 B2 | 4/2003 | Vaughn et al. | ............... | 502/214 |
| 6,660,682 B2 | 12/2003 | Cao et al. | ..................... | 502/214 |
| 6,717,025 B1 * | 4/2004 | Risch et al. | ................. | 585/804 |
| 2003/0018228 A1 | 1/2003 | Vaughn et al. | ............... | 585/500 |
| 2003/0181322 A1 | 9/2003 | Chang et al. | ................ | 502/214 |

FOREIGN PATENT DOCUMENTS

| | | |
|---|---|---|
| EP | 0 448 000 | 9/1991 |
| EP | 1 424 128 | 6/2004 |
| JP | 3303341 | 2/1994 |
| SU | 1472447 | 4/1989 |
| SU | 1558456 | 4/1990 |
| WO | WO 03/000412 | 1/2003 |
| WO | WO 03/000413 | 1/2003 |
| WO | WO 03/035549 | 1/2003 |
| WO | WO 2005/035120 | 4/2005 |

OTHER PUBLICATIONS

Abstract of RU 2173299, *"Preparation of Phosphated Crystalline Aluminum Oxide"*, Sep. 10, 2001.
Abstract of SU 1472447, *"Manufacture of High-Silica Zeolite ZSM-5"*, Apr. 15, 1989.
Abstract of SU 1558456, *"Method of Separating Heterogeneous Catalyst for Hydrogenation of Fatty Acids from Primary Fatty Alcohols of Hydrogenation Fraction"*, Apr. 23, 1990.
U. Hammon, et al, *"Formation of Ethene and Propene from Methanol on Zeolite ZSM-s: II. Preparation of Finished Catalysts and Operation of a Fixed-Bed Pilot Plant,"*, Applied Catalysis, 37 (1988) pp. 155-174.
Riekert, L. et al., *"Sorption und katalytische Reaktion in Silicoaluminaten und Silicoboraten der Pentasil-Klasse,"* Bundesministerium fur Forschung und Technologie, Institut fur Chemische Verfahrenstechnik der Universitot, BMFT-FB-T 82-175, Karlsruhe, Oct. 1982, 34 pages.

* cited by examiner

*Primary Examiner*—Glenn Caldarola
*Assistant Examiner*—In Suk Bullock

(57) ABSTRACT

The invention relates to a molecular sieve catalyst composition, to a method of making or forming the molecular sieve catalyst composition, and to a conversion process using the catalyst composition. In particular, the invention is directed to a conversion process for producing olefin(s), preferably ethylene and/or propylene, from a feedstock, preferably an oxygenate containing feedstock in the presence of a molecular sieve having been synthesized in the presence of a flocculant.

22 Claims, No Drawings

MOLECULAR SIEVE CATALYST COMPOSITION, ITS MAKING AND USE IN CONVERSION PROCESSES

FIELD OF THE INVENTION

The present invention relates to a molecular sieve catalyst composition, to a method of making or forming the molecular sieve catalyst composition, and to a conversion process using the catalyst composition.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in a variety of processes for making plastics and other chemical compounds.

The petrochemical industry has known that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming or a combination thereof.

Methanol, the preferred alcohol for light olefin production, is typically synthesized from the catalytic reaction of hydrogen, carbon monoxide and/or carbon dioxide in a reactor in the presence of a heterogeneous catalyst. For example, in one synthesis process methanol is produced using a copper/zinc oxide catalyst in a water-cooled tubular reactor. The preferred methanol conversion process is generally referred to as a methanol-to-olefin(s) process (MTO), where an oxygenate, typically mostly methanol, is converted into primarily ethylene and/or propylene in the presence of a molecular sieve.

There are many different types of molecular sieves well known to convert a feedstock, especially an oxygenate containing feedstock, into one or more olefin(s). Molecular sieves, such as zeolites or zeolite-type molecular sieves, carbons and oxides, are porous solids having pores of different sizes that selectively adsorb molecules that can enter the pores, and exclude other molecules that are too large. Examples of molecular sieves useful in converting an oxygenate into olefin(s) are: U.S. Pat. No. 5,367,100 describes the use of a well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; U.S. Pat. No. 4,310,440 describes producing light olefin(s) from an alcohol using a crystalline aluminophosphates, often represented by $ALPO_4$; and U.S. Pat. No. 4,440,871 describes silicoaluminophosphate molecular sieves (SAPO), one of the most useful molecular sieves for converting methanol into olefin(s).

Typically, molecular sieves are formed into molecular sieve catalyst compositions to improve their durability in commercial conversion processes. The collisions within a commercial process between catalyst composition particles themselves, the reactor walls, and other reactor systems cause the particles to breakdown into smaller particles called fines. The physical breakdown of the molecular sieve catalyst composition particles is known as attrition. Problems develop in the recovery systems because fines often exit the reactor in the product containing effluent stream. Catalyst compositions having a higher resistance to attrition generate fewer fines; this results in improved process operability, and less catalyst composition being required for a conversion process, and therefore, lower overall operating costs.

It is known that the way in which the molecular sieve catalyst compositions are made or formulated affects catalyst composition attrition. Molecular sieve catalyst compositions are formed by combining a molecular sieve and a matrix material usually in the presence of a binder. For example, PCT Patent Publication WO 03/000413 A1 published Jan. 3, 2003 discloses a low attrition molecular sieve catalyst composition using a synthesized molecular sieve that has not been fully dried, or partially dried, in combination in a slurry with a matrix material and/or a binder. Also, PCT Patent Publication WO 03/000412 A1 published Jan. 3, 2003 discusses a low attrition molecular sieve catalyst composition produced by controlling the pH of the slurry above the isoelectric point of the molecular sieve. U.S. Patent Application Publication No. U.S. 2003/0018228 published Jan. 23, 2003 shows making a low attrition molecular sieve catalyst composition by making a slurry of a synthesized molecular sieve, a binder, and optionally a matrix material, wherein 90 percent by volume of the slurry contains particles having a diameter less than 20 µm. U.S. patent application Ser. No. 10/178,455 filed Jun. 24, 2002, which is herein fully incorporated by reference, illustrates making an attrition resistant molecular sieve catalyst composition by controlling the ratio of a binder to a molecular sieve. U.S. Pat. No. 6,503,863 is directed to a method of heat treating a molecular sieve catalyst composition to remove a portion of the template used in the synthesis of the molecular sieve. U.S. Pat. No. 6,541,415 describes improving the attrition resistance of a molecular sieve catalyst composition that contains molecular sieve-containing recycled attrition particles and virgin molecular sieve and having been calcined to remove the template from the molecular sieve catalyst. U.S. Pat. No. 6,660,682 describes the use of a polymeric base to reduce the amount of templating agent required to produce a particular molecular sieve.

It is also known that in typical commercial processes that flocculants are used in the recovery of synthesized molecular sieves. These flocculants are known to facilitate the crystal recovery and to increase the yield of recovery of the synthesized molecular sieve typically in a large scale commercial process. However, the presence of a flocculate can affect the catalyst formulation, and in some cases flocculation can result in the formulation of catalyst compositions having lower attrition resistance and lower selectivity in various conversion processes.

Although these molecular sieve catalyst compositions described above are useful in hydrocarbon conversion processes, it would be desirable to have an improved molecular sieve catalyst composition having better selectivity to in particular prime olefins, especially ethylene and propylene.

SUMMARY OF THE INVENTION

This invention generally provides for a method of making or formulating a molecular sieve catalyst composition and to its use in a conversion process for converting a feedstock into one or more olefin(s).

In one embodiment the invention is directed to a process for producing one or more olefin(s), the process comprising the steps of: (a) introducing a feedstock to a reactor system in the presence of a formulated molecular sieve catalyst composition comprising a synthesized molecular sieve having been recovered in the presence of a flocculant; (b) withdrawing from the reactor system an effluent stream; and (c) passing the effluent stream through a recovery system recovering at least the one or more olefin(s). In one embodiment, the flocculent is a charged organic polymer. Preferably the synthesized molecular sieve is a metallo-aluminophosphate, a silicoaluminophosphate, an aluminophosphate, a chabazite (CHA) framework-type molecular sieve, or a CHA and AEI intergrowth or mixed framework-type molecular sieve.

In another preferred embodiment, the invention relates to a method for synthesizing a molecular sieve, the method comprising the steps of: (a) forming a synthesis mixture comprising two or more a silicon source, an aluminum source, a phosphorous source, and a templating agent; (b) introducing to the synthesis mixture a flocculent; and (c) recovering the synthesized molecular sieve. In one embodiment, the flocculant is a charged organic polymer. In another embodiment, the flocculant is selected from one or more of the group consisting of polyethylenimine. In yet another preferred embodiment, the synthesis mixture comprising three or more of a silicon source, an aluminum source, a phosphorous source, and a templating agent. In yet another embodiment, step (c) of recovering is one or more filtration step(s) or one or more filtration step(s) and washing step(s), or a combination of one or more of a centrifugation step(s), a washing step(s), and a filtration step(s). In yet another preferred embodiment of this embodiment, the amount of molecular sieve recovered in a single batch is greater than 250 Kg, preferably greater than 500 Kg, and most preferably greater than 1000 Kg.

DETAILED DESCRIPTION OF THE INVENTION INTRODUCTION

The invention is directed toward a molecular sieve catalyst composition, its making, and to its use in the conversion of a feedstock into one or more olefin(s). A formulated molecular sieve catalyst composition is typically formed from a slurry of the combination of a molecular sieve, a matrix material, and optionally, most preferably, a binder. It has been discovered that when recovering a molecular sieve in the presence of a flocculant in a molecular sieve synthesis process, the synthesized molecular sieve exhibits improved selectivity for primarily ethylene and propylene in a conversion process of one or more alcohols, more specifically methanol.

Molecular Sieves

Molecular sieves have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference. For additional information on molecular sieve types, structures and characteristics, see van Bekkum, et al., *Introduction to Zeolite Science and Practice, Second Completely Revised and Expanded Edition,* Volume 137, Elsevier Science, B. V., Amsterdam, Netherlands (2001), which is also fully incorporated herein by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEI, AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably an intergrowth thereof.

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves, preferably SAPO molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves based on silicon, aluminum, and phosphorous, and metal containing molecular sieves thereof, have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos.

4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,098,684 (MCM-41), 5,198,203 (MCM-48), 5,241,093, 5,304,363 (MCM-50), 5,493,066, 5,675,050, 6,077,498 (ITQ-1), 6,409,986 (ITQ-5), 6,419,895 (UZM-4), 6,471,939 (ITQ-12), 6,471,941 (ITQ-13), 6,475,463 (SSZ-55), 6,500,404 (ITQ-3), 6,500,998 (UZM-5 and UZM-6), 6,524,551 (MCM-58) and 6,544,495 (SSZ-57), 6,547,958 (SSZ-59), 6,555,090 (ITQ-36) and 6,569,401 (SSZ-64), all of which are herein fully incorporated by reference. Other molecular sieves are described in R. Szostak, *Handbook of Molecular Sieves*, Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves.

In one embodiment, the molecular sieve, as described in many of the U.S. Patents mentioned above, is represented by the empirical formula, on an anhydrous basis:

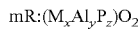

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Synthesis of a molecular sieve, especially a SAPO molecular sieve, its formulation into a SAPO catalyst, and its use in converting a hydrocarbon feedstock into olefin(s), is shown in, for example, U.S. Pat. Nos. 4,499,327, 4,677,242, 4,677,243, 4,873,390, 5,095,163, 5,714,662 and 6,166,282, all of which are herein fully incorporated by reference. Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, SAPO intergrowth molecular sieves are described in the U.S. patent application Ser. No. 09/924,016 filed Aug. 7, 2001, PCT Publication WO 02/070407 published Sep. 12, 2002 and PCT Publication WO 98/15496 published Apr. 16, 1998, which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the molar ratio of CHA to AEI is greater than 1:1.

Molecular Sieve Synthesis

Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds, and are placed in a sealed pressure vessel, optionally lined with an inert plastic such as polytetrafluoroethylene, and heated, under a crystallization pressure and temperature, at static or stirred conditions, until a crystalline material is formed in a synthesis mixture. Then, in a commercial process in particular, one or more flocculant(s) is added to the synthesis mixture. A liquid portion of the synthesis mixture is removed, decanted, or reduced in quantity. The remaining synthesis mixture containing the crystalline molecular sieve is then, optionally, contacted with the same or a different fresh liquid, typically with water, in a washing step, from once to many times depending on the desired purity of the supernatant, liquid portion, of the synthesis mixture being removed. It is also optional to repeat this process by adding in additional flocculent followed by additional washing steps. Then, the crystallized molecular sieve is recovered by filtration, centrifugation and/or decanting. Preferably, the molecular sieve is filtered using a filter that provides for separating certain crystal sized molecular sieve particles from any remaining liquid portion that may contain different size molecular sieve crystals.

In a preferred embodiment the molecular sieves are synthesized by forming a reaction product or synthesis mixture of a source of silicon, a source of aluminum, a source of phosphorous and an organic templating agent, preferably a nitrogen containing organic templating agent. This particularly preferred embodiment results in the synthesis of a silicoaluminophosphate crystalline material in a synthesis mixture. One or more flocculants are added to the synthesis mixture, and the crystallized molecular sieve is then removed or isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof. The preferred templating agent or template is a tetraethylammonium compound, tetraethyl ammonium hydroxide (TEAOH) and salts thereof, particularly when producing a SAPO molecular sieve.

Flocculants

When commercially synthesizing any of the molecular sieves discussed above, typically one or more chemical reagents are added to the crystallization vessel or synthesis reactor after crystallization is substantially complete, preferably complete. Optionally, in another embodiment, the synthesis mixture is transferred to another vessel separate from the reaction vessel or the vessel in which crystallization occurs, and a flocculant is then added to this other vessel from which the crystalline molecular sieve is ultimately recovered. These chemical reagents or flocculants are used to increase the recovery rate of the molecular sieve crystals and increase the yield of the synthesized molecular sieve crystals. While not wishing to be bound to any particular theory, these flocculants act either as (1) a surface charge modifier that results in the agglomeration of very small particles into larger aggregates of molecular sieve particles; or (2) surface anchors that bridge many small particles to form aggregates of molecular sieve particles. The aggregates of the molecular sieve crystals are then easily recovered by well known techniques such as filtration or through a filter press process.

Flocculants can be added at any point during or with any other source or templating agent used in the synthesis of any one of the molecular sieves discussed above. In one embodiment, flocculants are added to a molecular sieve synthesis mixture comprising one or more of a silicon source, a phosphorous source, an aluminum source, and a templating agent depending on the molecular sieve being synthesized. In the most preferred embodiment, the flocculant is added to the synthesis mixture after crystallization has occurred from the combination of one or more of a silicon source, a phosphorous source, an aluminum source, and a templating agent. The synthesized molecular sieve is then recovered by filtration, however, optionally, the synthesized molecular sieve is washed and additional flocculant is used to further aggregate any remaining synthesized molecular sieve from the liquid portion of the synthesis mixture.

There are many types of flocculants both inorganic and organic flocculants. Inorganic flocculants are typically aluminum or iron salts that form insoluble hydroxide precipitates in water. Non-limiting examples such as aluminum sulfate, poly (aluminum chloride), sodium aluminate, iron (III)-chloride, sulfate, and sulfate-chloride, iron (II) sulfate, and sodium silicate (activated silica). The major classes of flocculants are: (1) nonionic flocculant, for example, polyethylene oxide, polyacrylamide (PAM), partially hydrolyzed polyacrylamide (HPAM), and dextran; (2) cationic flocculant, for example, polyethyleneimine (PEI), polyacrylamide-co-trimethylammonium, ethyl methyl acrylate chloride (PTAMC), and poly (N-methyl-4-vinylpyridinium iodide); and (3) anionic flocculant, for example, poly (sodium acrylate), dextran sulfates, alum (aluminum sulfate), and/or high molecular weight ligninsulfonates prepared by a condensation reaction of formaldehyde with ligninsulfonates, and polyacrylamide. In a preferred embodiment, where the synthesis mixture includes the presence of water, it is preferable that the flocculant used is water soluble. Additional information on flocculation is discussed in T. C. Patton, *Paint Flow and Pigment Dispersion-A Rheological Approach to Coating and Ink Technology*, 2nd Edition, John Wiley & Sons, New York, p. 270, 1979, which is fully incorporated by reference.

In another embodiment, the flocculant is added to the synthesis mixture after crystallization in an amount of 0.01 to 10 wt % flocculant based on expected solid molecular sieve product yield, preferably between 0.05 to 5 wt % flocculant based on expected solid molecular sieve product yield, more preferably from 0.05 to 3 wt % based on expected solid molecular sieve product yield. In yet another embodiment, it is preferable that the product slurry and/or flocculant are diluted to obtain a volume of product slurry to volume of flocculant of between 1:1 and 10:1. Good mixing between the product slurry and the flocculant is also preferred. One can recover the flocculated sieve starting from the total mixture by centrifugation or filtration or one can allow the mixture to settle, decant the liquid, re-slurry with water, eventually repeatedly decant and re-slurry, and finally recover by centrifugation or filtration. The settling of the sieve can take from seconds to days; however, the settling can be accelerated by adding additional flocculant. The flocculant is typically added to the slurry at room temperature, and is preferably added as a solution. Should a solid flocculant be used then it is preferable that a substantially homogeneous flocculant solution is prepared by dissolving the solid flocculant in a medium.

In one preferred embodiment, the flocculant is a polymeric imine such as polyethyleneimine. In another preferred embodiment, the flocculant is represented by the formula: $(R-NH)_x$, where (R—NH) is a polymeric or monomeric unit where R contains from 1 to 20 carbon atoms, preferably from 1 to 10 carbon atoms, more preferably from 1 to 6 carbon atoms, and most preferably from 1 to 4 carbon atoms; x is an integer from 1 to 500,000.

In yet another embodiment, the flocculant is a polyethylenimine that is represented by the following general formula: $(-NHCH_2CH_2-)_m[-N(CH_2CH_2NH_2)CH_2CH_2-]_n$, wherein m is from 10 to 20,000, and n is from 0 to 2,000, preferably from 1 to 2000.

In another embodiment, the flocculant of the invention, preferably a polyethyleneimine, has an average molecular weight from about 500 to about 1,000,000, preferably from about 10,000 to about 800,000, more preferably from about 20,000 to about 750,000, and most preferably from about 50,000 to about 750,000.

Non-limiting examples of polyethylenimine flocculants include: epichlorohydrin modified polyethylenimine, ethoxylated polyethylenimine, polypropylenimine diamine dendrimers (DAB-Am-n), poly (allylamine) $[CH_2CH(CH_2NH_2)]_n$, poly (1,2-dihydro-2,2,4-trimethylquinoline), and poly (dimethylamine-co-epichlorohydrin-co-ethylenediamine).

In one embodiment, the flocculant is in an a solution, preferably an aqueous solution. In a further embodiment, the flocculant in the aqueous solution is diluted with water. Without being bound to any particular theory, it has been found that dilution of the molecular sieve slurry, preferably one recovered using a flocculant, prevents dissolution of the molecular sieve in the slurry. This benefit provides for a further improvement in yield, and allows for the slurry to be stored for an extended period of time.

A synthesis mixture comprising a molecular sieve and a flocculant has a pH depending on the composition of the molecular sieve. In a preferred embodiment, the synthesis mixture has a pH in the range of from 2 to 10, preferably in the range of from 4 to 9, and most preferably in the range of from 5 to 8. Generally, the synthesis mixture is sealed in a vessel and heated, preferably under autogenous pressure, to a temperature in the range of from about 80° C. to about 250° C., and more preferably from about 150° C. to about 180° C. The time required to form the crystalline molecular sieve is typically from immediately up to several weeks, the duration of which is usually dependent on the temperature; the higher the temperature the shorter the duration. Typically, the crystalline molecular sieve product is formed, usually in a slurry state, and then a flocculant is introduced to this slurry, the synthesis mixture. The crystalline molecular sieve is then recovered by any standard technique well known in the art, for example centrifugation or filtration. Alternatively, in another embodiment, the flocculant is introduced into the synthesis mixture directly.

Determination of the percentage of liquid or liquid medium and the percentage of flocculant and/or template for purposes of this patent specification and appended claims uses a Thermal Gravimetric Analysis (TGA) technique as follows: An amount of a molecular sieve material, the sample, is loaded into a sample pan of a Cahn TG-121 Microbalance, available from Cahn Instrument, Inc., Cerritos, Calif. During the TGA technique, a flow of 114 cc/min (STP) air was used. The sample is then heated from 25° C. to 180° C. at 30° C./min, held at 180° C. for 3 hours or until the weight of this sample becomes constant. The weight loss the percentage to the starting molecular sieve material is then treated as the percentage of the liquid or liquid medium. Subsequently, the sample is heated at 30° C./min from 180° C. to 650° C. and held at 650° C. for 2 hours. This weight loss as a percentage of the original sample weight during this treatment is regarded as the weight loss of the templating agent. The total weight loss as a percentage in terms of the original first sample weight during this entire TGA treatment is defined as Loss-On-Ignition (LOI).

In one embodiment, the isolated or separated crystalline product, the synthesized molecular sieve, is washed, typically using a liquid such as water, from one to many times, or in a semi-continuous or continuous way for variable lengths of time. The washed crystalline product is then optionally dried, preferably in air to a level such that the resulting, partially dried or dried crystalline product or synthesized molecular sieve has a LOI in the range of from about 0 weight percent to about 80 weight percent, preferably the range is from about greater than 1 weight percent to about 80 weight percent, more preferably from about 10 weight percent to about 70 weight percent, even more preferably from about 20 to about 60 weight percent, and most preferably from about 40 weight percent to about 60 weight percent. This liquid containing crystalline product, synthesized molecular sieve or wet filtercake, is then used below in the formulation of the molecular sieve catalyst composition of the invention.

The amount of flocculant introduced to the reactor vessel depends on the quantity of molecular sieve being recovered, the type of molecular sieve, the pH of the synthesis mixture, etc. In one embodiment, the amount of molecular sieve recovered is the range of from about 100 Kg to about 20,000 Kg or greater, preferably in the range of from 250 Kg to about 20,000 Kg, more preferably from about 500 Kg to about 20,000 Kg, and most preferably from about 1000 Kg to about 20,000 Kg. In another embodiment, the reactor vessel is capable of synthesizing an amount of molecular sieve in one batch or at one time in the range from about 100 Kg to about 20,000 Kg or greater, preferably greater than about 250 Kg to about 20,000 Kg, more preferably from about 500 Kg to about 20,000 Kg, and most preferably from about 1000 Kg to about 20,000 Kg.

Method for Making Molecular Sieve Catalyst Compositions

Once the molecular sieve is synthesized and heat treated as described above, depending on the requirements of the particular conversion process, the molecular sieve is then formulated into a molecular sieve catalyst composition, particularly for commercial use. The molecular sieves synthesized above are made or formulated into molecular sieve catalyst compositions by combining the synthesized molecular sieve(s), preferably after being thermally treated, with a binder, and optionally, but preferably, with a matrix material to form a formulated molecular sieve catalyst composition. It has been found that when thermally treating a synthesized molecular sieve having been recovered in the presence of a flocculant, prior to formulation, maintains or improves the formulated molecular sieve catalyst composition's resistance to attrition in various conversion processes.

This formulated composition is formed into useful shape and sized particles by well-known techniques such as spray drying, pelletizing, extrusion, and the like, spray drying being the most preferred. It is also preferred that after spray drying for example that the formulated molecular sieve catalyst composition is then calcined.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrate. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrate, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105-144 (1993), which is herein incorporated by reference. In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol AL20DW, available from Nyacol Nano Technologies, Inc., Ashland, Mass.

The synthesized molecular sieves described above, in a preferred embodiment, is combined with a binder and one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, non-active, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. In one embodiment, the matrix material, preferably any of the clays, are subjected to well known modification processes such as calcination and/or acid treatment and/or chemical treatment. In one preferred embodiment, the matrix material is kaolin, particularly kaolin having an average particle size from about 0.1 µm to about 0.6 µm with a $d_{90}$ particle size distribution of less than about 1 µm.

Upon combining the heat treated synthesized molecular sieve and the matrix material, optionally with a binder, in a liquid to form a slurry, mixing, preferably rigorous mixing, is needed to produce a substantially homogeneous mixture containing the heat treated synthesized molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The liquid containing the heat treated synthesized molecular sieve and matrix material, and the optional binder, are in the same or different liquid, and are combined in any order, together, simultaneously, sequentially, or a combination thereof. In the preferred embodiment, the same liquid, preferably water is used.

In one embodiment, the weight ratio of the binder to the molecular sieve is in the range of from about 0.1 to 0.5, more preferably in the range of from 0.11 to 0.48, even more preferably from 0.12 to about 0.45, yet even more preferably from 0.13 to less than 0.45, and most preferably in the range of from 0.15 to about 0.4. See for example U.S. patent application Ser. No. 10/178,455 filed Jun. 24, 2002, which is herein fully incorporated by reference.

The molecular sieve catalyst composition particles contains some water, templating agent or other liquid components, therefore, the weight percents that describe the solid content in the slurry are preferably expressed in terms exclusive of the amount of water, templating agent and/or other liquid contained within the particle. The most preferred condition for measuring solids content is on a calcined basis as, for example, as measured by the LOI procedure discussed above. On a calcined basis, the solid content in the slurry, more specifically, the molecular sieve catalyst composition particles in the slurry, are from about 20 percent by weight to 45 percent by weight molecular sieve, 5 percent by weight to 20 percent by weight binder, and from about 30 percent by weight to 80 percent by weight matrix material. See for example U.S. Patent Application Publication No. U.S. 2003/0018228 published Jan. 23, 2003, which is herein fully incorporated by reference.

In another embodiment, the heat treated molecular sieve is combined with a binder and/or a matrix material forming a slurry such that the pH of the slurry is above or below the isoelectric point of the molecular sieve. Preferably the slurry comprises the molecular sieve, the binder and the matrix material and has a pH different from, above or below, preferably below, the IEP of the molecular sieve, the binder and the matrix material. In an embodiment, the pH of the slurry is in the range of from 2 to 7, preferably from 2.3 to 6.2; the IEP of the molecular sieve is in the range of from 2.5 to less than 7, preferably from about 3.5 to 6.5; the IEP of the binder is greater than 10; and the IEP of the matrix material is less than 2. See PCT Patent Publication WO 03/000412 A1 published Jan. 3, 2003, which is herein fully incorporated by reference.

As the slurry is mixed, the solids in the slurry aggregate preferably to a point where the slurry contains solid molecular sieve catalyst composition particles. It is preferable that these particles are small and have a uniform size distribution such that the $d_{90}$ diameter of these particles is less than 20 µm, preferably less than 15 µm, more preferably less than 10 µm, and most preferably about 7 µm. The $d_{90}$ for purposes of this patent application and appended claims means that 90 percent by volume of the particles in the slurry have a particle diameter lower than the $d_{90}$ value. For the purposes of this definition, the particle size distribution used to define the $d_{90}$ is measured using well known laser scattering techniques using a Honeywell (Microtrac Model 3000 particle size analyzer from Microtrac, Inc., Largo, Fla.).

In one embodiment, the slurry of the synthesized molecular sieve, binder and matrix material is mixed or milled to achieve a sufficiently uniform slurry of sub-particles of the molecular sieve catalyst composition to form a formulation composition that is then fed to a forming unit that produces the molecular sieve catalyst composition or formulated molecular sieve catalyst composition. In a preferred embodiment, the forming unit is a spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, any one or a combination of the slurries described above, more particularly a slurry of the synthesized molecular sieve, matrix material, and binder, is co-fed to the spray dryer with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas. Generally, the size of the microspheres is controlled to some extent by the solids content of the slurry. However, control of the size of the catalyst composition and its spherical characteristics are controllable by varying the slurry feed properties and conditions of atomization.

Other methods for forming a molecular sieve catalyst composition is described in U.S. Pat. No. 6,509,290 (spray drying using a recycled molecular sieve catalyst composition), which is herein incorporated by reference.

In a preferred embodiment, once the molecular sieve catalyst composition is formed, to further harden and/or activate the formed catalyst composition, the spray dried molecular sieve catalyst composition or formulated molecular sieve catalyst composition is calcined. Typical calcination temperatures are in the range of from about 500° C. to about 800° C., and preferably from about 550° C. to about 700° C., preferably in a calcination environment such as air, nitrogen, helium, flue gas (combustion product lean in oxygen), or any combination thereof. Calcination time is typically dependent on the degree of hardening of the molecular sieve catalyst composition and ranges from about 15 minutes to about 20 hours at a temperature in the range of from 500° C. to 700° C.

In one embodiment, the attrition resistance of a molecular sieve catalyst composition is measured using an Attrition Rate Index (ARI), measured in weight percent catalyst composition attrited per hour. ARI is measured by adding 6.0 g of catalyst composition having a particle size distribution ranging from 53 microns to 125 microns to a hardened steel attrition cup. Approximately 23,700 cc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent the catalyst composition that has broken apart through attrition. The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst in grams charged to the attrition cup expressed on per hour basis is the ARI, in weight percent per hour (wt. %/hr). ARI is represented by the formula: $ARI = C/(B+C)/D$ multiplied by 100%, wherein B is weight of catalyst composition left in the cup after the attrition test, C is the weight of collected fine catalyst particles after the first hour of attrition treatment, and D is the duration of treatment in hours after the first hour attrition treatment.

In one embodiment, the molecular sieve catalyst composition or formulated molecular sieve catalyst composition has an ARI less than 10 weight percent per hour, preferably less than 5 weight percent per hour, more preferably less than 2 weight percent per hour, and most preferably less than 1 weight percent per hour.

Process For Using the Molecular Sieve Catalyst Compositions

The molecular sieve catalyst compositions described above are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve catalyst compositions described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene. Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition of the invention into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking. The most preferred process is generally referred to as gas-to-olefins (GTO) or alternatively, oxygenate-to-olefins (OTO) or methanol-to-olefins (MTO). In a MTO or an OTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference. The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

Reactor System

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

The feedstock entering the reactor system is preferably converted, partially or fully, in the first reactor zone into a gaseous effluent that enters the disengaging vessel along with a coked or further coked molecular sieve catalyst composition. In the preferred embodiment, cyclone(s) within the disengaging vessel are designed to separate the molecular sieve catalyst composition, preferably a coked or further coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor. Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference. Other processes for converting an oxygenate to olefin(s) are described in U.S. Pat. No. 5,952,538 (WHSV of at least 20 $hr^{-1}$ and a Temperature Corrected Normalized Methane Selectivity (TCNMS) of less than 0.016), EP-0 642 485 B1 (WHSV is from 0.01 $hr^{-1}$ to about 100 $hr^{-1}$, at a temperature of from about 350° C. to 550° C.), and PCT WO 01/23500 published Apr. 5, 2001 (propane reduction at an average catalyst feedstock exposure of at least 1.0), which are all herein fully incorporated by reference.

The coked molecular sieve catalyst composition is withdrawn from the disengaging vessel, preferably by one or more cyclones(s), and introduced to the regeneration system.

Regeneration System

The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition. By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336-337), which is herein incorporated by reference.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa). The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

Other regeneration processes are described in U.S. Pat. Nos. 6,023,005 (coke levels on regenerated catalyst), 6,245,703 (fresh molecular sieve added to regenerator) and 6,290,916 (controlling moisture), U.S. patent application Ser. No. 09/587,766 filed Jun. 6, 2000 (cooled regenerated catalyst returned to regenerator), U.S. patent application Ser. No. 09/785,122 filed Feb. 16, 2001 (regenerated catalyst contacted with alcohol), and PCT WO 00/49106 published Aug. 24, 2000 (cooled regenerated catalyst contacted with by-products), which are all herein fully incorporated by reference.

The gaseous effluent is withdrawn from the disengaging system and is passed through a recovery system.

Recovery System

There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like. Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water. In one embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system to remove various non-limiting examples of contaminants and by-products include generally polar compounds such as water, alcohols, carboxylic acids, ethers, carbon oxides, ammonia and other nitrogen compounds, chlorides, hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249-271 and 894-899, which is herein incorporated by reference.

Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Included in the recovery systems of the invention are reaction systems for converting the products contained within the effluent gas withdrawn from the reactor or converting those products produced as a result of the recovery system utilized. Suitable well known reaction systems as part of the recovery system primarily take lower value products such as the $C_4$ hydrocarbons, butene-1 and butene-2 and convert them to higher value products. Non-limiting examples of these types of reaction systems include U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading $C_3$, $C_4$ and $C_5$ Olefinic Streams*, Pet. & Coal, Vol. 37, No. 4 (1995) (dimerizing or oligomerizing propylene, butylene and pentylene), which are all herein fully incorporated by reference.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent gas fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

Integrated Processes

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas. Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol. The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference. In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Light Olefin Usage

The light olefin products, especially the ethylene and the propylene, are useful in polymerization processes that include solution, gas phase, slurry phase and a high pressure processes, or a combinations thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

EXAMPLES

In order to provide a better understanding of the present invention including representative advantages thereof, the following examples are offered.

LOI and ARI are specified in this patent specification.

Example A

There are numerous methods well known for making molecular sieves. The following is an example preparation of a molecular sieve, particularly a silicoaluminophosphate molecular sieve. Procedures for making a similar molecular sieve used in the examples below is described in PCT Publication WO 02/070407 published Sep. 12, 2002, which is fully incorporated by reference.

To a solution of 63.94 grams of phosphoric acid (85% in water) and 51.22 grams of de-mineralized water, 4.15 grams of Ludox AS 40 (40% silica) was added upon stirring. Then, 116.71 grams of TEAOH (35% in water) was added. Finally 37.75 grams of pseudoboehmite alumina (Condea Pural SB) was added together with 6.22 grams of de-mineralized water. This slurry solution, a synthesis mixture, had a composition expressed as the molar ratio:

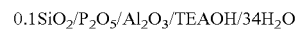

$$0.1 SiO_2/P_2O_5/Al_2O_3/TEAOH/34H_2O$$

This synthesis mixture was then mixed until homogeneous and put into a 300 ml stainless steel autoclave. The autoclave was mounted on a rotating axis in an oven. The axis was rotated at 60 rpm and the oven was heated in 8 hours to 175° C. The autoclave was kept at this temperature for 12 hours. After crystallization a milky suspension with a pH of 10 was obtained, the slurry was then homogenized before dividing into 3 Parts:

Comparative Part 1: 50.04 g of the slurry above. No flocculant was added. Part 2: 50.0 g of the slurry above and 19.26 g prepared 5 wt % PEI (polyethyleneimine) (MW 750,000) solution. (Preparation of 5 wt % PEI solution: 2 g of 50 wt % PEI (Aldrich, MW 750,000) and 18 g of bi-distilled water was mixed with a spatula until homogeneous). Part 3: 50.02 g of the slurry above and 19.69 g prepared 5 wt % lower molecular weight PEI (MW 50,000 to 60,000) solution. (Preparation of PEI solution: 2.07 g of 50 wt % PEI (Aldrich, MW 50,000 to 60,000) and 18.1 g of bi-distilled water was mixed with a spatula until homogeneous). Parts 2 and 3 with the PEI flocculant immediately became viscous after addition of the flocculent. Comparative Part 1 and Part 2 were stirred on a magnetic stirrer plate for 25 minutes before washing. During that time Part 3 was left without stirring on the bench and allowed to settle. This resulted in a thick white slurry settling to the bottom with a substantially clear liquid on top. Then, Part 3 was also stirred and washed.

Each of Comparative Part 1, Parts 2 and 3 were washed three (3) times with about 180 g of distilled water for 10 minutes in a centrifuge at 3500 rpm. The wash water of Comparative Part 1was hazy while that of Parts 2 and Parts 3 were clear and colorless. The recovered products, the synthesized molecular sieves, were dried overnight in air at 120° C. The dried weights of the synthesized molecular sieves were: Comparative Part 1: 11.81 g, Part 2: 15.15 g and Part 3: 15.05 g.

Example 2

Conversion Process

The three synthesized molecular sieves above, Comparative Part 1 and Parts 2 and 3, were tested in a conversion process where in the oxygenated feed stock was methanol, and the conversion conditions were 25 WHSV, 25 psig (172 kPag) pressure, and at a temperature 450° C. The results of which are reported in the following Table 1.

TABLE 1

| Products | Comparative Part 1 | Part 2 | Part 3 |
|---|---|---|---|
| C2= (ethylene) | 32.34 | 31.59 | 31.79 |
| C3= (propylene) | 40.41 | 41.58 | 42.38 |
| C2= + C3= | 72.75 | 73.16 | 74.17 |
| C3⁰ (Propane) | 0.77 | 0.58 | 0.54 |
| ²C4⁺ | 23.59 | 23.60 | 23.04 |
| ¹Life Time | 19.01 | 17.15 | 17.26 |

$^1$Life Time is measured as grams of methanol converted per gram of molecular sieve.
$^2$C4$^+$ includes butene-1, butene-2, and higher carbon number hydrocarbons.

While the present invention has been described and illustrated by reference to particular embodiments, those of ordinary skill in the art will appreciate that the invention lends itself to variations not necessarily illustrated herein. For example, it is contemplated that one or more molecular sieves are recoverable in the presence of one or more flocculants. For this reason, then, reference should be made solely to the appended claims for purposes of determining the true scope of the present invention.

We claim:

1. A process for producing one or more olefin(s), the process comprising the steps of:
   (a) introducing a feedstock to a reactor system in the presence of a molecular sieve catalyst composition comprising a synthesized molecular sieve having been recovered in the presence of a polymeric amine flocculant;
   (b) withdrawing from the reactor system an effluent stream; and
   (c) passing the effluent gas through a recovery system recovering at least the one or more olefin(s).

2. The process of claim 1 wherein the feedstock comprises one or more oxygenates.

3. The process of claim 1 wherein the synthesized molecular sieve is synthesized from a synthesis mixture comprising a silicon source, a phosphorous source and an aluminum source, optionally in the presence of a templating agent.

4. The process of claim 1 wherein the formulated molecular sieve catalyst composition further comprises a binder and a matrix material.

5. The process of claim 1 wherein the flocculant has a molecular weight (MW) in the range of from 10,000 to 800,000.

6. The process of claim 1 wherein the flocculant is present in an amount of about 0.01 to 10 wt % flocculant based on the total weight of the synthesized molecular sieve.

7. The process of claim 1 wherein the flocculant is represented by the formula: $(R-NH)_x$, where (R—NH) is a polymeric or monomeric unit where R contains from 1 to 20 carbon atoms, and x is an integer from 1 to 500,000.

8. The process of claim 1 wherein the flocculant is represented by the formula: $(-NHCH_2CH_2-)_m[-N(CH_2CH_2NH_2)CH_2CH_2-]_n)$, wherein m is from 10 to 20,000, and n is from 0 to 2,000.

9. The process of claim 1 wherein the synthesized molecular sieve is selected from one or more of the group consisting of: a metalloaluminophosphate, a silicoaluminophosphate, an aluminophosphate, a CHA framework-type molecular sieve, an AEI framework-type molecular sieve and a CHA and AEI intergrowth or mixed framework-type molecular sieve.

10. The process of claim 1 wherein the greater than 1000 Kg of one or more olefin(s) is being produced.

11. The process of claim 1 wherein the one or more olefin(s) include ethylene and propylene.

12. The process of claim 1 wherein the synthesized molecular sieve is formulated into a formulated molecular sieve catalyst composition, the formulated molecular sieve catalyst composition comprising the synthesized molecular sieve, a matrix material, and optionally a binder.

13. An integrated process for making one or more olefin(s), the integrated process comprising the steps of:
   (a) passing a hydrocarbon feedstock to a syngas production zone to producing a synthesis gas stream;
   (b) contacting the synthesis gas stream with a catalyst to form an oxygenated feedstock; and
   (c) converting the oxygenated feedstock into the one or more olefin(s) in the presence of a molecular sieve catalyst composition, the molecular sieve catalyst composition comprising a synthesized molecular sieve having been recovered in the presence of a polymeric amine flocculant.

14. The integrated process of claim 13 wherein the process further comprises the step of: (d) polymerizing the one or more olefin(s) in the presence of a polymerization catalyst into a polyolefin.

15. The integrated process of claim 13 wherein the oxygenated feedstock comprises methanol, the olefin(s) include ethylene and propylene, and the synthesized molecular sieve is a silicoaluminophosphate molecular sieve.

16. The integrated process of claim 13 wherein the flocculant has a molecular weight (MW) in the range of from 10,000 to 800,000.

17. The integrated process of claim 13 wherein the flocculant is present in an amount of about 0.01 to 10 wt % flocculant based on the total weight of the molecular sieve synthesized.

18. The integrated process of claim 13 wherein the flocculant is represented by the formula: $(R-NH)_x$, where (R—NH) is a polymeric or monomeric unit where R contains from 1 to 20 carbon atoms, and x is an integer from 1 to 500,000.

19. The integrated process of claim 13 wherein the flocculant is represented by the formula: $(-NHCH_2CH_2-)_m$ $[-N(CH_2CH_2NH_2)CH_2CH_2-]_n)$, wherein m is from 10 to 20,000, and n is from 0 to 2,000.

20. The integrated process of claim 13 wherein the flocculant is a polyethyleneimine.

21. The integrated process of claim 13 wherein the molecular sieve catalyst composition further comprises a matrix material, and optionally a binder.

22. The integrated process of claim 13 wherein the flocculant is present in an amount of about 0.01 to 10 wt % flocculant based on the total weight of the synthesized molecular sieve.

* * * * *